(12) United States Patent
Krautkremer et al.

(10) Patent No.: US 10,709,877 B2
(45) Date of Patent: Jul. 14, 2020

(54) MEDICAL BALLOON WITH REINFORCING MEMBER

(71) Applicant: BOSTON SCIENTIFIC SCIMED, INC., Maple Grove, MN (US)

(72) Inventors: Daniel Lee Krautkremer, Plymouth, MN (US); Katherine M. Prindle, Robbinsdale, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 252 days.

(21) Appl. No.: 15/789,324

(22) Filed: Oct. 20, 2017

(65) Prior Publication Data

US 2018/0117287 A1     May 3, 2018

Related U.S. Application Data

(60) Provisional application No. 62/414,325, filed on Oct. 28, 2016.

(51) Int. Cl.
*A61M 25/10* (2013.01)

(52) U.S. Cl.
CPC ........ *A61M 25/1034* (2013.01); *A61M 25/10* (2013.01); *A61M 25/1002* (2013.01); *A61M 25/1029* (2013.01); *A61M 2025/1084* (2013.01)

(58) Field of Classification Search
CPC .. A61M 2025/1084; A61M 2025/1075; A61M 25/10; A61M 25/1029; A61M 25/1034; A61M 2025/1031; A61M 2025/1088; A61M 25/0014; A61M 25/104; A61F 2/958

See application file for complete search history.

(56) References Cited

U.S. PATENT DOCUMENTS

| 5,868,779 | A | 2/1999 | Ruiz |
| 2003/0120207 | A1 | 6/2003 | Wang |
| 2004/0015183 | A1* | 1/2004 | Lim ........................ A61L 29/06 |
| | | | 606/194 |

(Continued)

FOREIGN PATENT DOCUMENTS

| EP | 1846074 A2 | 10/2007 |
| JP | 2005512694 A | 5/2005 |

(Continued)

OTHER PUBLICATIONS

International Search Report and Written Opinion dated Jan. 19, 2018 for International Application No. PCT/US2017/507651.

*Primary Examiner* — Katherine M Shi (74) *Attorney, Agent, or Firm* — Seager, Tufte & Wickhem LLP (57) ABSTRACT

Catheter assemblies and methods for making and using catheter assemblies are disclosed. An example a catheter assembly includes a catheter shaft and a balloon attached to the catheter shaft. The balloon includes a body and a proximal waist portion. The proximal waist portion has a proximal end. The catheter assembly also has a fiber braid including one or more individual filaments disposed along the balloon. The fiber braid has a proximal end aligned with the proximal end of the waist portion. The catheter assembly also has a polymer sleeve disposed on the catheter shaft, wherein in the polymer sleeve abuts the proximal end of the balloon waist and the proximal end of the braid.

14 Claims, 7 Drawing Sheets

(56) References Cited

U.S. PATENT DOCUMENTS

| | | | |
|---|---|---|---|
| 2005/0238833 A1* | 10/2005 | Wang | A61M 25/1029 |
| | | | 428/36.91 |
| 2006/0271093 A1 | 11/2006 | Holman et al. | |
| 2009/0012610 A1 | 1/2009 | Olson et al. | |
| 2012/0277783 A1 | 11/2012 | Cummins et al. | |
| 2017/0143943 A1* | 5/2017 | Prindle | A61M 25/10 |

FOREIGN PATENT DOCUMENTS

| | | |
|---|---|---|
| JP | 200854135 A | 9/2009 |
| WO | 2003053508 A1 | 7/2003 |
| WO | 2006130194 A2 | 12/2006 |

* cited by examiner

MEDICAL BALLOON WITH REINFORCING MEMBER

CROSS-REFERENCE TO RELATED APPLICATIONS

This application claims the benefit of priority under 35 U.S.C. § 119 to U.S. Provisional Application Ser. No. 62/414,325, filed Oct. 28, 2016, the entirety of which is incorporated herein by reference.

TECHNICAL FIELD

The disclosure relates to intravascular medical devices such as medical balloons and methods of making the same.

BACKGROUND

Medical balloons may be utilized in a variety of medical treatments. For example, in an angioplasty procedure, a medical balloon may be used to expand a diseased body lumen. Medical balloons may also be used to deliver and deploy an expandable endoprosthesis, such as a stent, at a target site within a body lumen.

Medical balloons may be delivered to a target site by advancing a balloon catheter over a guidewire to the target site. In some cases, the pathway to a target site may be tortuous and/or narrow. Upon reaching the site, the balloon may be expanded by injecting a fluid into the interior of the balloon. Expanding the balloon may radially expand the stenosis such that normal blood flow may be restored through the body lumen.

In some instances, a high pressure medical balloon may be utilized when treating a particular target site (e.g., a stenosis). Further, in some instances a balloon may be utilized which includes a reinforcing/strengthening material. For example, to achieve the high pressure, some medical balloons may include one or more fiber braids designed to increase the radial strength of the balloon. Examples disclosed herein may include medical devices and methods for manufacturing those devices having a fiber braid.

SUMMARY

This disclosure provides design, material, manufacturing method, and use alternatives for medical devices. An example catheter assembly includes a catheter shaft and a balloon attached to the catheter shaft. The balloon includes a body and a proximal waist portion, the proximal waist portion having an proximal end. The catheter assembly further includes a fiber braid including one or more individual filaments disposed along the balloon. The fiber braid has a proximal end aligned with the proximal end of the waist portion. The catheter assembly further includes a polymer sleeve disposed on the catheter shaft, wherein in the polymer sleeve abuts the proximal end of the balloon waist and the proximal end of the braid.

Alternatively or additionally to any of the embodiments above, wherein the polymer sleeve includes a distal end, and a portion of the distal end of the polymer sleeve extends into the proximal end of the waist portion.

Alternatively or additionally to any of the embodiments above, wherein the polymer sleeve includes a distal end, and a portion of the distal end of the polymer sleeve extends into the proximal end of the braid.

Alternatively or additionally to any of the embodiments above, wherein one or more portions of the polymer sleeve is wicked along one or more individual filaments of the braid within the waist portion.

Alternatively or additionally to any of the embodiments above, wherein the polymer sleeve is thermally bonded to the waist portion.

Alternatively or additionally to any of the embodiments above, wherein the polymer sleeve is thermally bonded to the braid.

Alternatively or additionally to any of the embodiments above, wherein the waist portion and the polymer sleeve are thermally bonded to catheter shaft.

Alternatively or additionally to any of the embodiments above, wherein the balloon waist comprises a polymer.

Alternatively or additionally to any of the embodiments above, wherein the polymer of the balloon waist is different from the polymer that comprises the polymer sleeve.

Alternatively or additionally to any of the embodiments above, wherein the polymer of the balloon waist has a melting point that is greater than the melting point of the polymer of the polymer sleeve.

Alternatively or additionally to any of the embodiments above, wherein the melting point of the polymer of the balloon waist matches the melting point of the polymer of the polymer sleeve.

Alternatively or additionally to any of the embodiments above, wherein the fiber braid comprises a material having a melting point greater than the melting point of the waist or the polymer of the polymer sleeve.

Alternatively or additionally to any of the embodiments above, wherein the polymer sleeve is interlocked with one or more of the filaments of the fiber braid.

Another example catheter assembly includes:
a catheter shaft;
a balloon attached to the catheter shaft, the balloon including a body and a waist portion, the waist portion having an end;
a fiber braid including a plurality of individual filaments disposed along the body and waist portion of the balloon, the individual filaments having ends aligned with the end of the waist portion; and
a polymer sleeve disposed on the catheter shaft, the polymer sleeve abutting the end of the balloon waist, wherein one or more portions of the polymer sleeve extend along the individual filaments of the braid.

An example method of making a catheter assembly includes:
disposing a fiber braid about a balloon, the balloon comprising a waist portion and a body portion, the waist portion and the fiber braid each having an end, wherein the end of the waist is aligned with the end of the braid;
disposing the balloon on a catheter shaft;
disposing a polymer sleeve on a catheter shaft abutting the end of the waist portion;
applying heat to the at least a portion of the balloon waist and polymer sleeve to thermally bond the polymer sleeve to the balloon waist, wherein a portion of the polymer sleeve extends into the waist portion.

Alternatively or additionally to any of the embodiments above, wherein disposing the polymer sleeve on the catheter shaft includes overlapping the polymer sleeve with the end of the waist portion.

Alternatively or additionally to any of the embodiments above, wherein overlapping the polymer sleeve with the end of the waist portion includes position the polymer sleeve radially inward of the waist portion.

Alternatively or additionally to any of the embodiments above, wherein a portion of the polymer sleeve wicks along one or more fibers of the fiber braid.

Alternatively or additionally to any of the embodiments above, wherein thermally bonding the polymer sleeve to the balloon waist further includes interlocking the polymer sleeve with one or more fibers of the fiber braid.

Alternatively or additionally to any of the embodiments above, wherein the polymer sleeve extends into the waist portion such that the polymer sleeve at least partially surrounds at least one or more fibers of the fiber braid.

The above summary of some embodiments is not intended to describe each disclosed embodiment or every implementation of the present disclosure. The FIG.s, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As used herein, the terms "proximal" and "distal" refer to that which is closest to the user such as a surgeon and that which is furthest from the user respectively.

As discussed above, medical balloons may be utilized in a variety of medical treatments. For example, in an angioplasty procedure, a medical balloon may be used to widen a diseased body lumen, such as a arteries in the vasculature. A medical balloon may also be used to deliver and deploy an expandable endoprosthesis, such as a stent, at a target site within a body lumen.

Medical balloons may be utilized in a variety of medical treatments. For example, in an angioplasty procedure, a medical balloon may be used to expand a diseased body lumen. Medical balloons may also be used to deliver and deploy an expandable endoprosthesis, such as a stent, at a target site within a body lumen.

Medical balloons may be delivered to a target site by advancing a balloon catheter over a guidewire to the target site. In some cases, the pathway to a target site may be tortuous and/or narrow. Upon reaching the site, the balloon may be expanded by injecting a fluid into the interior of the balloon. Expanding the balloon may radially expand the stenosis such that normal blood flow may be restored through the body lumen.

In some instances it may be desirable to utilize high pressure medical balloons when treating a particular target site (e.g., a stenosis). Further, in some instances it may be desirable to utilize a balloon which includes a reinforcing/strengthening material. For example, to achieve the high pressure, some medical balloons may include one or more fiber braids designed to increase the radial strength of the balloon. Examples disclosed herein may include medical devices and methods for manufacturing those devices having a fiber braid.

Figure 1:
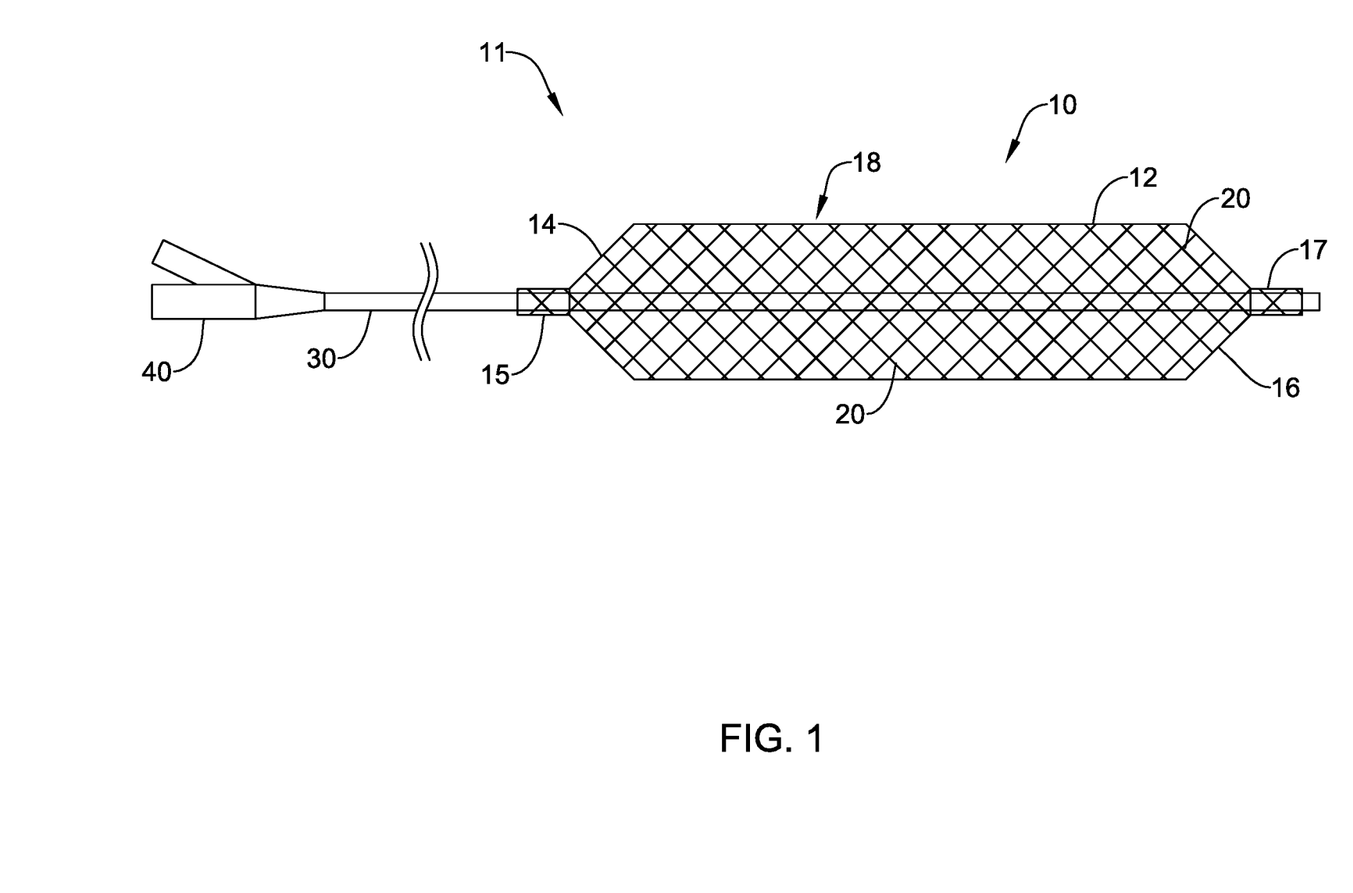
FIG. 1 illustrates an example medical device.

FIG. 1 shows example balloon catheter system 11. System 11 may include an expandable medical balloon 10 mounted to a distal end of a catheter shaft 30. The catheter shaft 30 may extend from a manifold assembly 40 positioned at a proximal end of the catheter shaft 30. Balloon 10 is shown having a body portion 12, a proximal cone portion 14, a distal cone portion 16, a proximal waist portion 15, and a distal waist portion 17. Balloon 10 may be secured to the catheter shaft 30 at the proximal waist 15 and distal waist portions 17, respectively.

Catheter shaft 30 may include a guidewire lumen (not shown) extending therein and an inflation lumen (not shown) extending therein for inflation of balloon 10. Alternatively, the catheter shaft 30 may include an inner tubular member defining a guidewire lumen and an outer tubular member disposed around the inner tubular member, whereby an inflation lumen may be defined between the inner tubular member and the outer tubular member.

Additionally, and as illustrated in FIG. 1, balloon 10 may include a fiber braid 18 disposed thereon. Fiber braid 18 may be disposed along an outer surface of balloon 10. However, this is not intended to be limiting. Rather, it is contemplated that braid 18 may be partially or fully embedded in the wall of balloon 10. It can further be appreciated that fiber braid 18 may extend around the circumference of balloon 10. Specifically, braid 18 may wrap around the circumference of balloon 10.

Fiber braid 18 may include one or more filaments 20. Further, fiber braid 18 may be configured such that the one or more filaments 20 are braided, wound, wrapped, woven, etc. around the outer surface and/or partially or fully within the wall of balloon 10. Additionally, filaments 20 may be braided, wound, wrapped, woven, etc. in a variety of configurations around the outer surface and/or partially or fully within the wall of balloon 10.

In some examples, the inner surface of at least one of the proximal waist portion 15 and/or the distal waist portion 17 are bonded (e.g., thermally, adhesively, etc.) to an outer surface of a portion of the catheter shaft 30 prior to bonding of the fiber braid 18 to the proximal waist portion 15 and/or the distal waist portions 17. As used herein, thermal bonding refers to the melting of materials or a portion thereof by applying heat, laser, welding or some combination thereof, to obtain a mixing or bonding of the materials at the material interface. Alternatively, an inner surface of the fiber braid 18 may be adhesively bonded to an outer surface of the proximal waist portion 15 and distal waist portion 17. Additionally, it is contemplated the fiber braid 18 may be attached to balloon 10 via any suitable process, including heat welding, laser welding, etc.

Further, a suitable adhesive may be employed for bonding the fiber braid 18 to the balloon 10, including proximal waist portion 15, and distal waist portion 17. The adhesive may include, but is not limited to, for example, thermoset adhesives that suitably cure either via a chemical reaction or irradiation. Specific examples of suitable thermoset adhesives include moisture cure and radiation cure such as ultraviolet (UV) radiation cure, e-beam, and the like. In some embodiments, the adhesive is a thermoset cyanoacrylate adhesive. A particular example is Loctite 4011 available from Henkel Adhesives.

Figure 2:
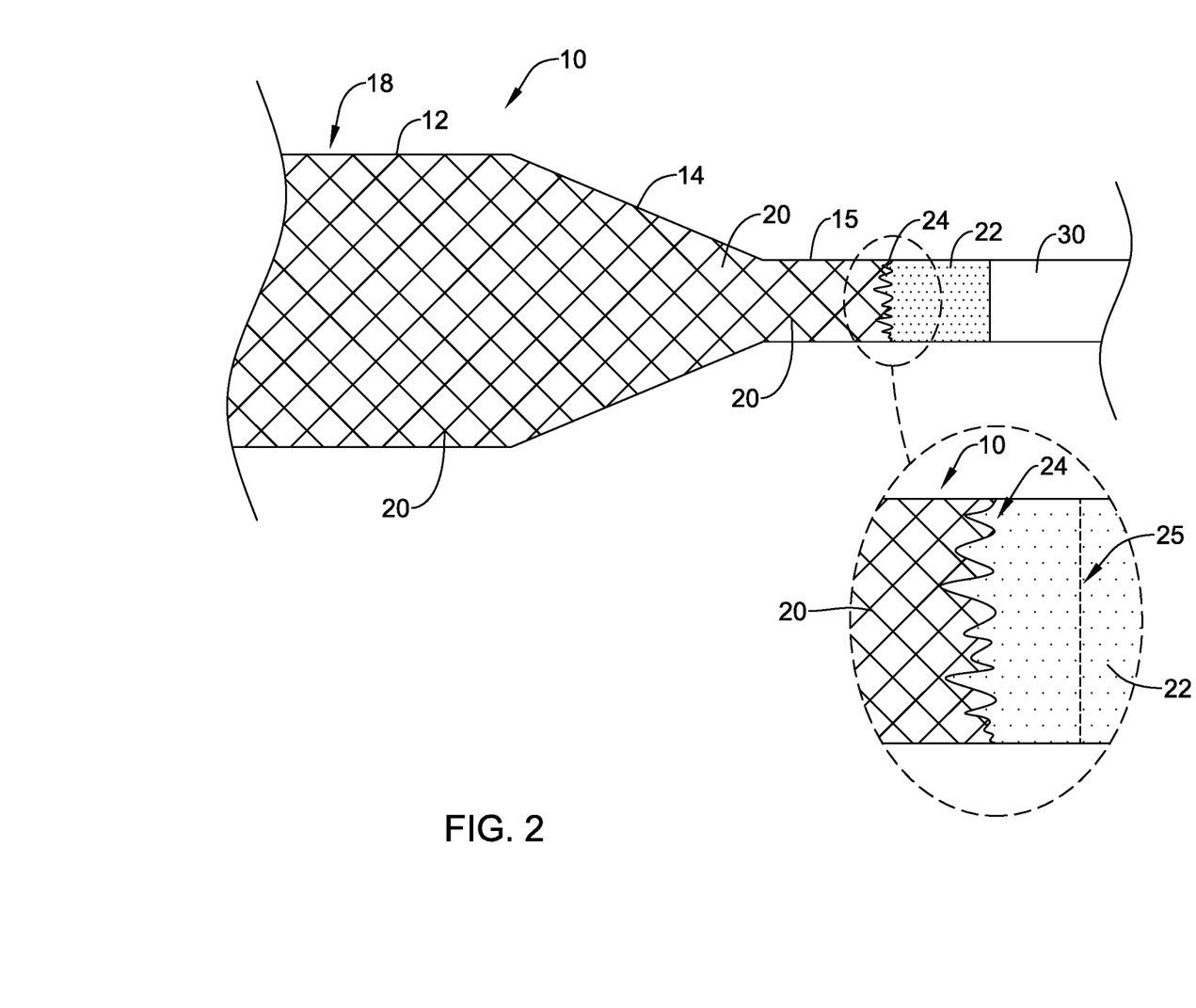
FIG. 2 illustrates a portion of the medical device of FIG. 1.

FIG. 2 illustrates the proximal portion of an example balloon 10 bonded to a portion of catheter shaft 30. As shown in FIG. 2, one of more filaments 20 of fiber braid 18 may extend in a proximal direction from the balloon body 12, along the proximal balloon cone 14 and further along the proximal balloon waist 15. Additionally, FIG. 2 illustrates a bonding sleeve 22 disposed along the proximal portion of the proximal waist 15. As will be described in detail below, bonding sleeve 22 may be designed to cover, encapsulate, embed and/or seal the proximal portion of the braid 18 located at the proximal portion of the proximal waist 15.

The detailed view shown in FIG. 2 illustrates that a portion of bonding sleeve 22 may extend along a proximal portion of the proximal waist 15. As will be described in greater detail below, the bonding sleeve 22 may be designed such that it extends in a proximal-to-distal direction along at least a portion the proximal waist 15. Specifically, the detailed view of FIG. 2 shows that bonding sleeve 22 may extend over the end of the proximal waist 15 of balloon 10 (the end of the proximal waist 15 of balloon 10 is depicted as dashed line 25 in the detailed view of FIG. 2). Additionally, the detailed view of FIG. 2 illustrates that bonding sleeve 22 may wick and/or flow in a distal-to-proximal direction along the fibers 20 of braid 18. A distal portion 24 of bonding sleeve 22 is depicted in both the detailed and non-detailed views of FIG. 2. It can be appreciated the distal portion 24 of bonding sleeve 22 may or may not terminate a uniform distance from end of proximal waist 15. For example, it can be appreciated that as bonding sleeve 22 wicks and/or flows in a distal-to-proximal direction along the fibers 20 of braid 18, that some portions of bonding sleeve may advance further along the braid 18 than other adjacent portions (as depicted by the jagged line of distal portion 24 of bonding sleeve 22).

Figure 3:
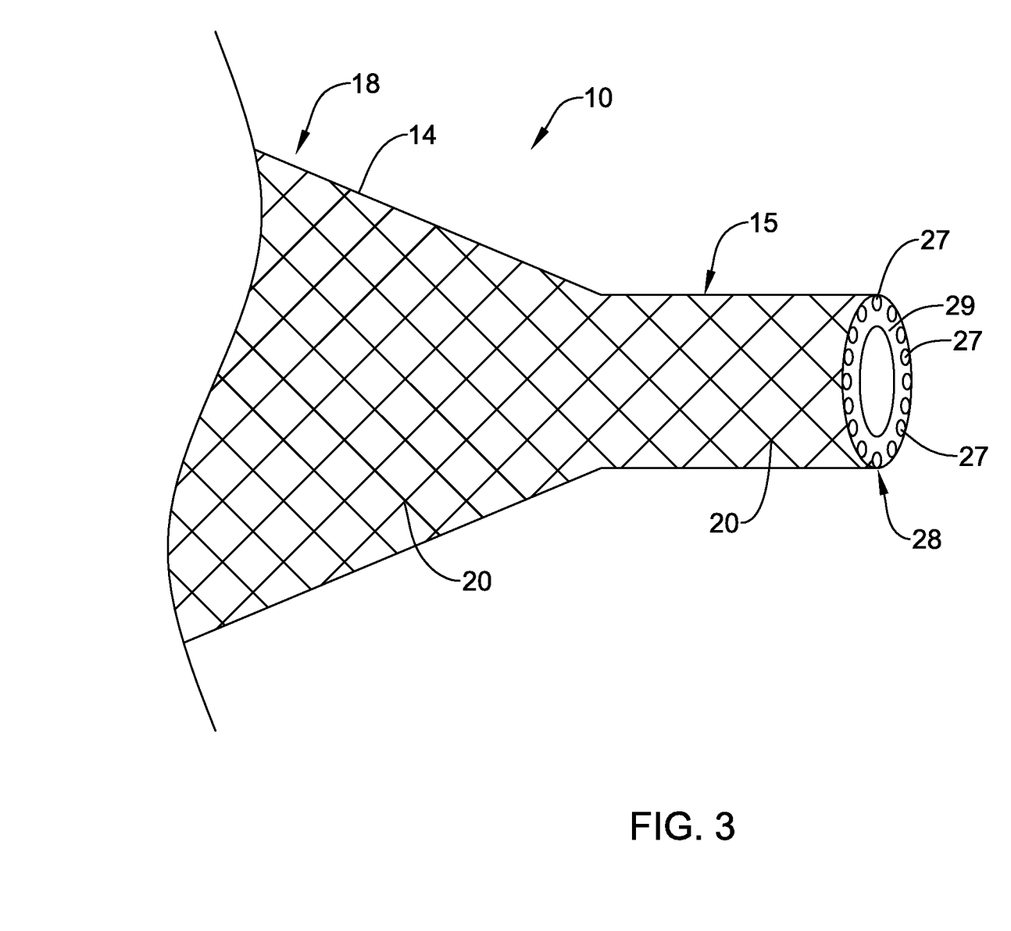
FIG. 3 illustrates a portion of the medical device of FIG. 1.

FIG. 3 illustrates an example step in manufacturing catheter system 11. FIG. 3 shows that the proximal waist 15 may be trimmed to an appropriate length prior to bonding the proximal waist 15 of balloon 10 to catheter shaft 30. FIG. 3 illustrates that the proximal waist 15 of balloon 10 has been cleanly cut along proximal edge 28. Further, FIG. 3 illustrates that the trimming process of proximal balloon waist 15 may reveal a proximal face 29 of the proximal waist 15. Further, the proximal face 29 shows the ends 27 of one or more fibers 20 of braid 18. The ends 27 of fibers are positioned along the proximal face 29. In other words, the trimming process may result in the end 28 of the proximal balloon waist aligning with the ends 27 of the one or more fibers 20 of braid 18.

As shown in FIG. 3, it can be appreciated the trimming process may result in one or more of fibers 20 becoming exposed along either the proximal face 29 and/or along the outer surface of proximal balloon waist 15. Further, the trimming process may cause the ends 27 of the one or more fibers 20 to become unraveled, frayed, exposed, released and/or unattached to the proximal waist 15 and/or proximal face 29. In some instances, the ends 27 of one or more fibers 20 may extend radially outward of the outer diameter of the proximal waist 15. Further, it can be appreciated that it may be undesirable to have the ends 27 of one or more fibers 20 extending/projecting away from balloon waist 15 as they may interfere with a medical devices and/or delivery systems utilized in conjunction with catheter system 11. For example, the ends 27 of the one or more fibers 20 may interfere with a stent being positioned on balloon 10. Therefore, it may be desirable to recapture, cover, encase, encapsulate, overlay and/or seal the ends 27 of the one or more fibers 20 within another material. For example, it may be desirable to recapture, cover, encase, encapsulate, overlay and/or seal the ends 27 of the one or more fibers 20 with a bonding sleeve 22 as described above.

Figure 4:
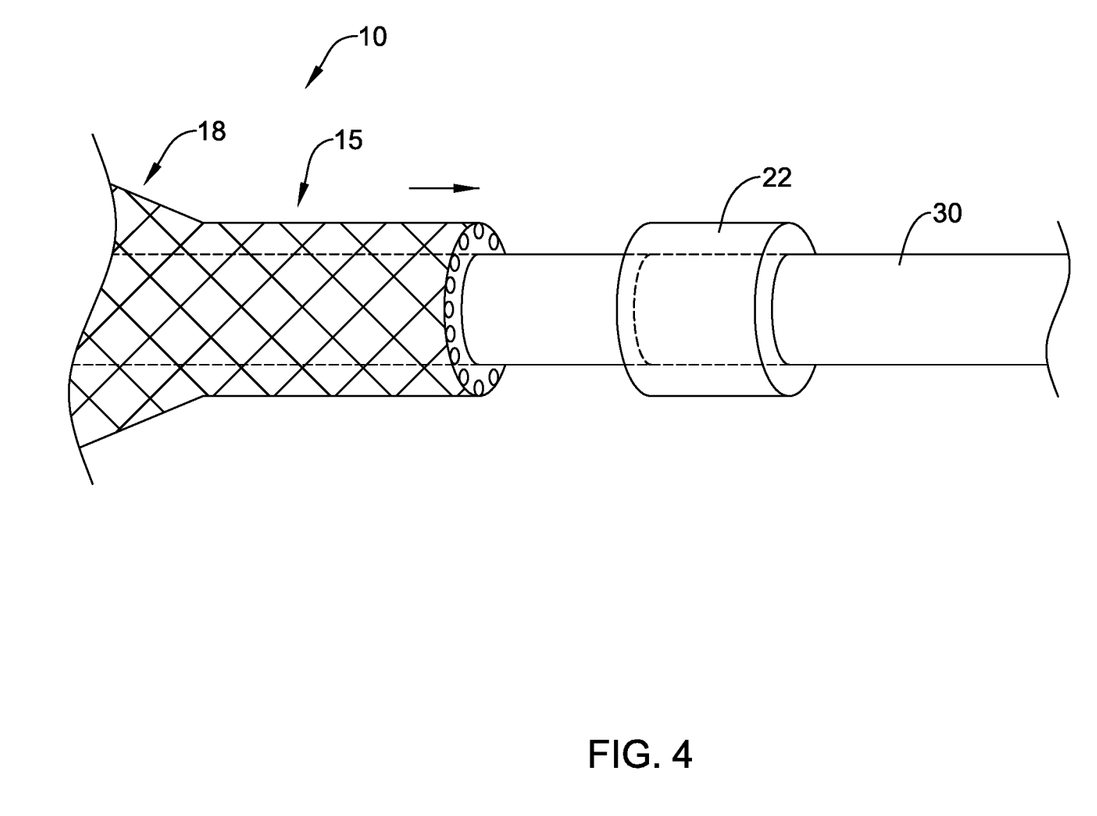
FIG. 4 illustrates an example manufacturing process for an example medical device.

FIG. 4 shows an example assembly step in manufacturing catheter system 11. FIG. 4 shows a bonding sleeve 22 (prior to being melted) being positioned on catheter shaft 30. Further, FIG. 4 shows catheter shaft 30 extending through the proximal waist 15. Additionally, FIG. 4 shows balloon 10 (including proximal waist 15) being advanced toward bonding sleeve 22. However, while FIG. 4 illustrates balloon 10 (including proximal waist 15) being advanced toward bonding sleeve 22, it is also contemplated that bonding sleeve 22 may be advanced toward proximal waist 15.

Figure 5:
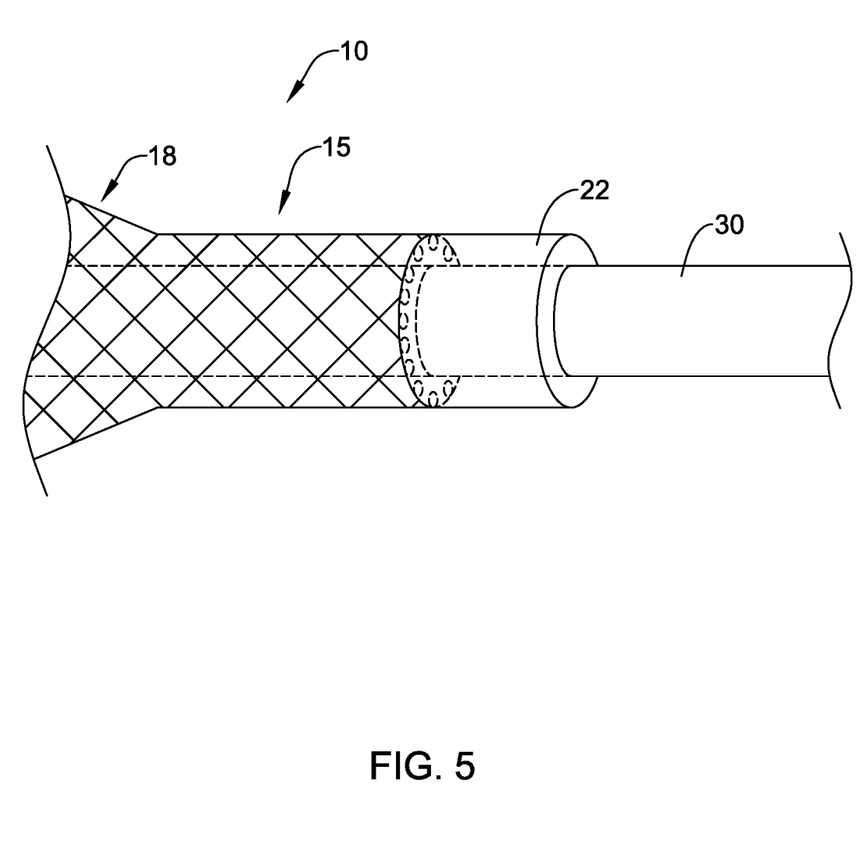
FIG. 5 illustrates an example manufacturing process for an example medical device.

FIG. 5 shows another example assembly step in manufacturing catheter system 11. FIG. 5 shows that bonding sleeve 22 and/or and proximal waist 22 have been moved to a position in which it abuts proximal waist 15 of balloon 10. In other words, FIG. 5 illustrates that a portion of the proximal face 29 (shown in FIG. 3) of proximal waist 15 may create a butt joint (e.g., a joint in which the proximal face of the proximal waist 15 may contact a distal face of the bonding sleeve 22) prior to the bonding process. However, this is not intended to be limiting. Other arrangements of proximal waist 15, bonding sleeve 22 and catheter shaft 30 are contemplated. For example, it is contemplated that the distal portion of bonding sleeve 22 may overlap with the proximal end of the proximal waist 15 prior to the bonding process.

Figure 6:
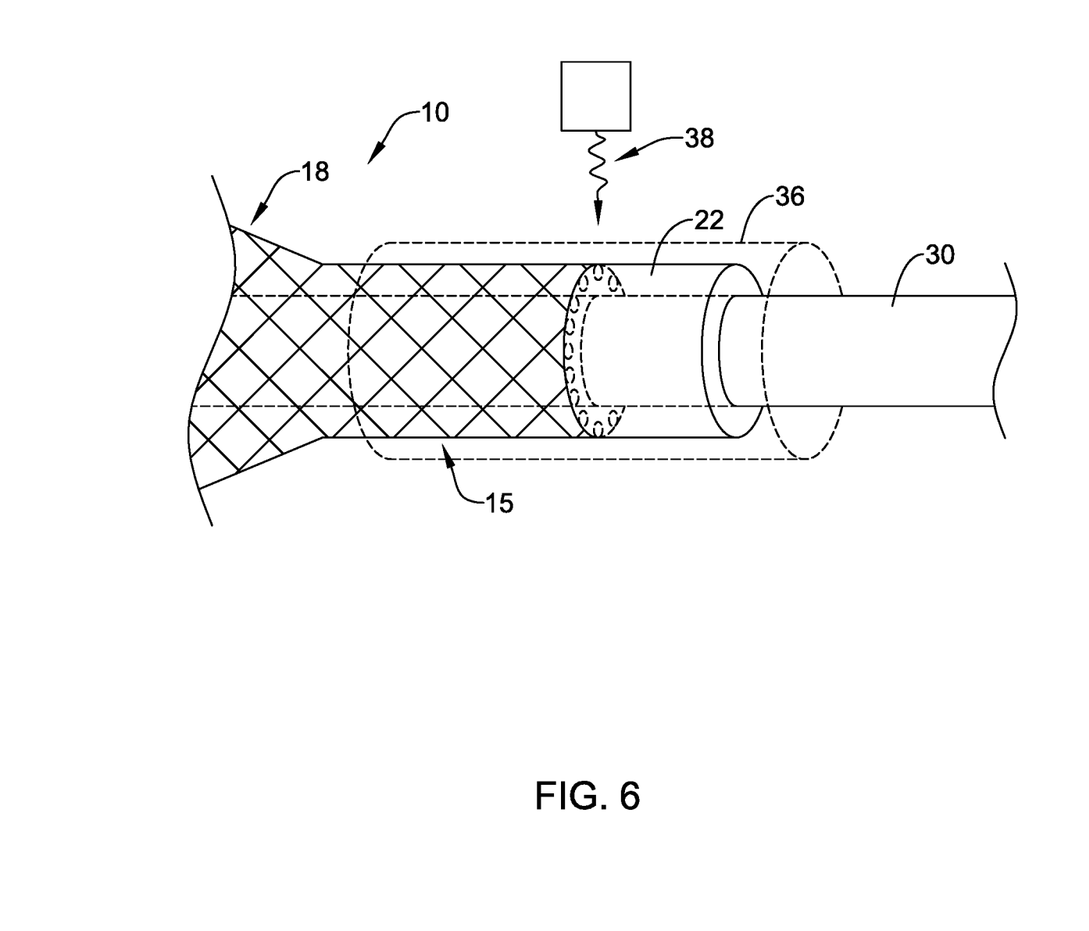
FIG. 6 illustrates an example manufacturing process for an example medical device.

FIG. 6 shows another example assembly step in manufacturing catheter system 11. FIG. 6 shows an example process for melting bonding sleeve 22 such that it melts and/or reflows over the proximal end of the proximal waist 15. FIG. 6 illustrates a piece of heat shrink 36 positioned over the proximal waist 15, the bonding sleeve 22 and the catheter shaft 30. Additionally, FIG. 6 shows energy 38 (e.g., laser energy, thermal energy, etc.) being applied to the heat shrink 36. Further, the heat shrink 36 may transfer/disperse the energy to the bonding sleeve 22, proximal waist 15 and/or the catheter shaft 30, thereby thermally bonding the bonding sleeve 22 to the proximal waist 15 and/or the catheter shaft 30.

It can be appreciated that the melting points of the balloon material, fibers 20, bonding sleeve 22, and catheter shaft may be the same or they may be different. For example, it may be desirable for the bonding sleeve 22 to be made from a material having a melting point which is lower than the balloon material, fibers 20 and/or bonding sleeve 22. For example, all or a portion of balloon 10 (including proximal balloon waist 15) may be manufactured from Pebax®, which has an approximate melt temperature of 220° C. All or a portion of catheter shaft 30 may be manufactured from Grilamid L20®, for example, which has an approximate melt temperature of 178° C. All or a portion of fibers 20 may include Vectran®, for example, which has an approximate melt temp of 330° C. and does not melt at bonding temps.

It can be appreciated that the catheter system 11 illustrated and described with respect to FIG. 2 may be the configuration of the catheter system 11 after processing the catheter system as described in FIG. 6. In other words, the illustration and description of the bonding sleeve and proximal waist interface in FIG. 2 may represent the catheter after it undergoes the processing and bonding steps as described in FIGS. 3-6.

Figure 7:
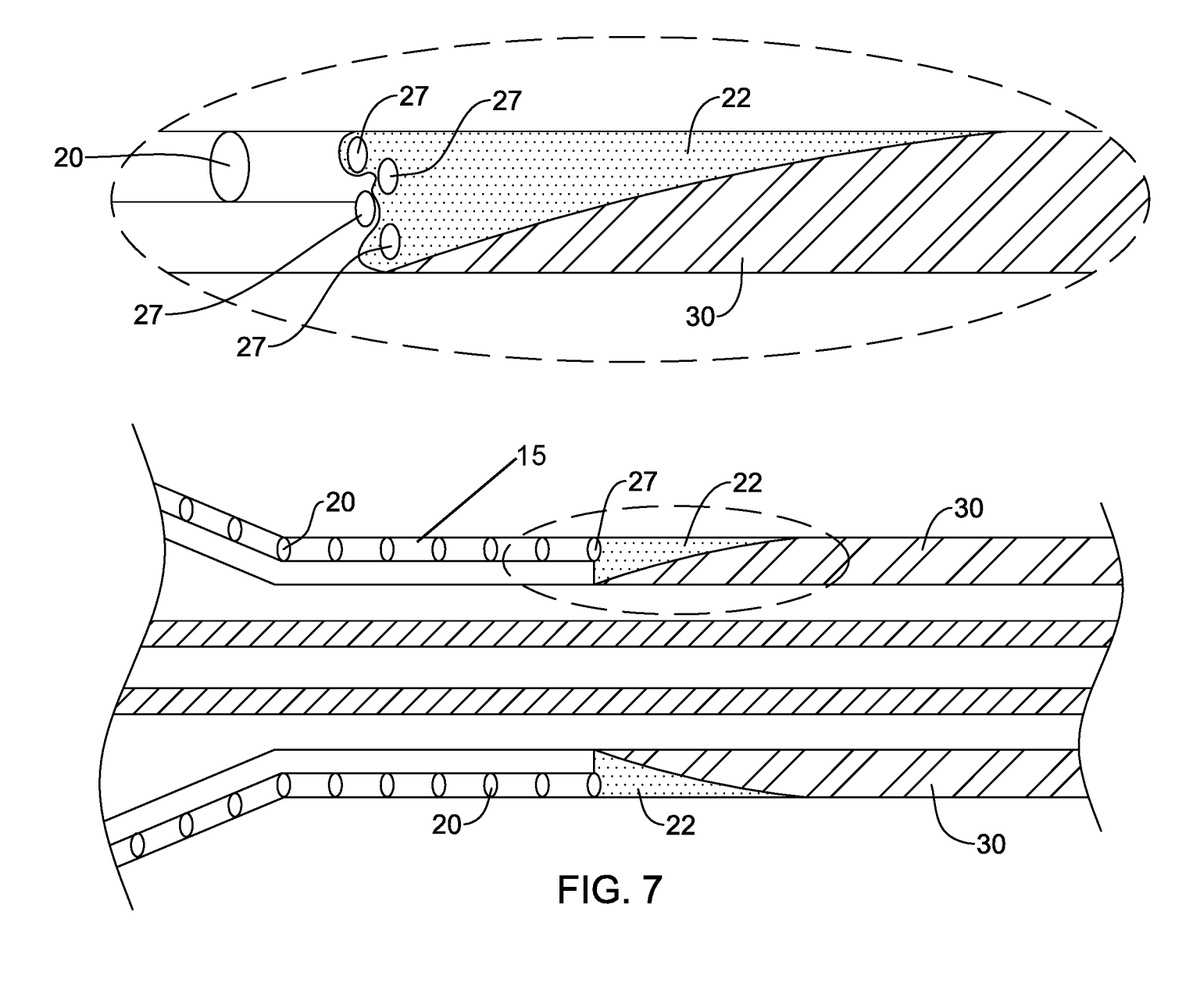
FIG. 7 illustrates a cross-section of an example medical device.

FIG. 7 illustrates a cross-sectional view of the proximal waist 15, bonding sleeve 22 and catheter shaft 30 after the bonding step has been performed as described in FIG. 6. FIG. 7 illustrates one or more ends 27 of fibers 20 being captured, covered, encased, encapsulated, overlaid and/or sealed by the material of bonding sleeve 22. For example, FIG. 7 shows that after energy 38 is applied during the assembly step as described in FIG. 6, the bonding sleeve 22 may melt and/or reflow into and around the ends 27 of fibers 20 of braid 18. It is noted that FIG. 7 does not show heat shrink 36 (shown in FIG. 6) positioned over the proximal waist 15 and/or bonding sleeve 22 because heat shrink 36 is removed from the proximal waist 15 and bonding sleeve 22 once sufficient energy has been applied to reflow the proximal waist 15 and bonding sleeve 22 into the cross-section view shown in FIG. 7. In other words, bonding sleeve 22 may melt and/or reflow into the proximal waist 15 which includes fibers 20 of fiber braid 18. It can be further appreciated the trimming of balloon 10 as described in FIG. 3 may results in cavities, channels, openings and/or spaces existing between fibers 20. Therefore, the cavities, channels, openings and/or spaces may permit the bonding sleeve 22 material to wick up one or more fibers 20 of braid 18, thereby surrounding, covering, encasing, encapsulating, overlaid and/or sealing the fibers 20 within the bonding material 22.

Balloon 10 may be pre-formed by radial expansion of a tubular parison, which is optionally also longitudinally stretched. The extruded parison may be radially expanded in a mold or by free-blowing. Alternatively, the parison may be pre-stretched longitudinally before expansion or reformed in various ways to reduce thickness of the balloon cone and waist regions prior to radial expansion. The blowing process may utilize pressurization under tension, followed by rapid dipping into a heated fluid; a sequential dipping with differing pressurization; a pulsed pressurization with compressible or incompressible fluid, after the material has been heated. Heating may also be accomplished by heating the pressurization fluid injected into the parison.

Balloon 10 may be formed from balloon materials including compliant, semi-compliant, and non-compliant materials. These materials may include thermoplastic polymers, elastomers, and non-elastomers. Such materials may include low, linear low, medium, and high density polyethylenes, polypropylenes, and copolymers and terpolymers thereof; polyurethanes; polyesters and copolyesters; polycarbonates; polyamides; thermoplastic polyimides; polyetherimides; polyetheretherketones (PEEK) and PES (polyether sulfone); and copolymers and terpolymers thereof. Physical blends and copolymers of such materials may also be used. Examples of polyesters include, but are not limited to, polyethylene terephthalate (PET), polyethylene naphthalate (PEN), polybutylene terephthalate, and copolymers thereof. Examples of polyamides which may be used include nylon 6, nylon 64, nylon 66, nylon 610, nylon 610, nylon 612, nylon 46, nylon 9, nylon 10, nylon 11, nylon 12, and mixtures thereof. Examples of suitable polyurethanes include, but are not limited to, aromatic polyether-based thermoplastic polyurethanes (TPUs) such as those available under the tradename of Tecothane® from Thermedics; thermoplastic polyurethane elastomer available under the tradename of Pellethane®, such as Pellethane® 2363-75D from Dow Chemical Co.; and high strength engineering thermoplastic polyurethane available under the tradename of Isoplast®, such as Isoplast® 301 and 302 available from Dow Chemical Co.

In some embodiments, the balloon 10 may be formed from poly (ether-block-amide) copolymers. The polyamide/polyether block copolymers are commonly identified by the acronym PEBA (polyether block amide). The polyamide and polyether segments of these block copolymers may be linked through amide linkages, or ester linked segmented polymers (e.g., polyamide/polyether polyesters). Such polyamide/polyether/polyester block copolymers are made by a molten state polycondensation reaction of a dicarboxylic polyamide and a polyether diol. The result is a short chain polyester made up of blocks of polyamide and polyether. Polymers of this type are commercially available under the tradename of Pebax® from Arkema. Specific example are the "33" series polymers with hardness 60 and above, Shore D scale, for example, Pebax® 6333, 7033, and 7233. These polymers are made up of nylon 12 segments and poly (tetramethylene ether) segments linked by ester groups.

Polyester/polyether segmented block copolymers may also be employed herein. Such polymers are made up of at least two polyester and at least two polyether segments. The polyether segments are the same as previously described for the polyamide/polyether block copolymers useful in the disclosure. The polyester segments are polyesters of an aromatic dicarboxylic acid and a two to four carbon diol.

In some embodiments, the polyether segments of the polyester/polyether segmented block copolymers are aliphatic polyethers having at least 2 and no more than 10 linear saturated aliphatic carbon atoms between ether linkages. Ether segments may have 4-6 carbons between ether linkages, and can be poly(tetramethylene ether) segments. Examples of other polyethers which may be employed in place of or in addition to tetramethylene ether segments include polyethylene glycol, polypropylene glycol, poly(pentamethylene ether) and poly(hexamethylene ether). The hydrocarbon portions of the polyether may be optionally branched. An example is the polyether of 2-ethylhexane diol. Generally such branches will contain no more than two carbon atoms. The molecular weight of the polyether segments is suitably between about 400 and 2,500, such as between 650 and 1000.

In some embodiments, the polyester segments of the polyester/polyether segmented block copolymers are polyesters of an aromatic dicarboxylic acid and a two to four carbon diol. Suitable dicarboxylic acids used to prepare the polyester segments of the polyester/polyether block copolymers are ortho-, meta-, or para-phthalic acid, napthalenedicarboxylic acid, or meta-terphenyl-4,4'-dicarboxylic acids. Specific examples of polyester/polyether block copolymers are poly(butylene terephthalate)-block-poly(tetramethylene oxide) polymers such as Arnitel® EM 740, sold by DSM Engineering Plastics, and Hytrel® polymers, sold by DuPont, such as Hytrel® 8230.

The above lists are intended for illustrative purposes only, and not as a limitation on the present disclosure. It is within purview of those of ordinary skill in the art to select other polymers without departing from the scope of this disclosure.

Balloon 10 may be capable of being inflated to relative high pressures. For example, the balloon 10 may be inflated to pressures up to about 20 atm or more, or up to about 25 atm or more, or up to about 30 atm or more, or up to about 40 atm or more, or up to about 45 atm or more, or up to about 50 atm or more, or about 20-50 atm, or about 25-40 atm, or about 30-50 atm. At such elevated pressures, the bond between the proximal waist portion 15 and the catheter shaft 30 (as well as the bond between the distal waist portion 17 and the catheter shaft 30) is maintained. Furthermore, the fluid tight bond between the fiber braid 18 and the balloon 10 is also maintained at these elevated pressures.

In some embodiments, the balloon 10 is formed from a compliant material. In some embodiments, the balloon 10 is formed from an elastomer, such as a block copolymer elastomer. The block copolymer elastomer may be a poly(ether-block-amide) copolymer. The balloon can also be formed of layers, for example, an inner layer formed of a first polymer material and an outer layer formed from a second polymer material different than the first polymer material. For example, in some embodiments, the inner layer may be formed from an elastomeric polymer material, for example, a block copolymer elastomer, and the outer layer is formed from a non-elastomeric polymer material. In some embodiments, the inner layer is formed of a poly(ether-block-amide) copolymer; and the outer layer is formed of a polyamide.

The fiber braid 18 may be formed from a suitable polymer material. General classes of suitable fiber braid materials include, for example, polyesters, polyolefins, polyamides, polyurethanes, liquid crystal polymers, polyimides, and mixtures thereof. More specific examples include, but are not limited to, polyesters such as polyethylene terephthalate (PET), polybutylene terephthalate (PBT), and polytrimethylene terephthalate (PTT). Polyamides include nylons and aramids such as Kevlar®. Liquid crystal polymers include Vectran®. Polyolefins include ultrahigh molecular weight polyethylene, such as Dyneema® sold by DSM Dyneema BVm Heerlen, Netherlands, Spectra® fibers, sold by Honeywell, and very high density polyethylene, and polypropylene fibers. Elastomeric fibers can be used in some cases.

In some embodiments, the fiber braid 18 comprises an ultra high molecular weight polyethylene (UHMPE). Commercially available UHMPEs include, but are not limited to, Dyneema® fiber available from DSM Dyneema BVm Heerlen, Netherlands, Spectra® fiber available from Honeywell in Morristown and Pegasus UHMWPE fiber available from Pegasus Materials in Shanghai, China. The UHMWPE fibers provide excellent strength and modulus with a small filament size to provide excellent balloon coverage and maintaining a minimal profile. However, when melted, the fibers lose their high molecular orientation and consequently, may also lose their bond tensile strength at the proximal waist portion 15 and/or the distal waist portion 17 of the balloon 10 at a thermal bond interface.

Additionally coatings may be optionally applied to the balloon 10, such as between the outer surface of the balloon 10 and the fiber braid 18, over the outer surface of the fiber braid 18 or both. In some embodiments, the coating includes a thermoplastic elastomer. In other instances, the coating includes a thermoplastic polyurethane. In some instances, the coating of a thermoplastic polyurethane may be applied to the balloon 10 using a suitable technique (e.g., dip coating, spray coating, rolling, or the like) prior to braiding and is also applied to the balloon/braid after braiding.

The catheter shaft 30 and/or other parts of catheter system 11 (e.g., bonding sleeve 22) may be formed from any suitable shaft material. Examples include, but are not limited to, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the shaft material mixture can contain up to about 6 percent LCP. In some embodiments, the catheter shaft 30 is formed from a polyamide, for example Grilamid® which is commercially available from EMS-Grivory.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A catheter assembly, comprising:
   a catheter shaft;
   a balloon attached to the catheter shaft, the balloon including a body and a proximal waist portion, the proximal waist portion having a proximal end;
   a fiber braid including one or more individual filaments disposed along the balloon, the fiber braid having a proximal end aligned with the proximal end of the waist portion; and
   a polymer sleeve disposed on the catheter shaft, wherein the polymer sleeve abuts the proximal end of the balloon waist and the proximal end of the braid such that an outer diameter of the catheter assembly remains substantially constant along the proximal waist portion of the balloon and an entirety of the polymer sleeve.

2. The catheter assembly of claim 1, wherein the polymer sleeve includes a distal end, and a portion of the distal end of the polymer sleeve extends into the proximal end of the waist portion.

3. The catheter assembly of claim 1, wherein the polymer sleeve includes a distal end, and a portion of the distal end of the polymer sleeve extends into the proximal end of the braid.

4. The catheter assembly of claim 1, wherein one or more portions of the polymer sleeve is wicked along one or more individual filaments of the braid within the waist portion.

5. The catheter assembly of claim 1, wherein the polymer sleeve is thermally bonded to the waist portion.

6. The catheter assembly of claim 1, wherein the polymer sleeve is thermally bonded to the braid.

7. The catheter assembly of claim 1, wherein the waist portion and the polymer sleeve are thermally bonded to catheter shaft.

8. The catheter assembly of claim 1, wherein the balloon waist comprises a polymer.

9. The catheter assembly of claim 8, wherein the polymer of the balloon waist is different from the polymer that comprises the polymer sleeve.

10. The catheter assembly of claim 8, wherein the polymer of the balloon waist has a melting point that is greater than the melting point of the polymer of the polymer sleeve.

11. The catheter assembly of claim 8, wherein the melting point of the polymer of the balloon waist matches the melting point of the polymer of the polymer sleeve.

12. The catheter assembly of claim 1, wherein the fiber braid comprises a material having a melting point greater than the melting point of the waist or the polymer of the polymer sleeve.

13. The catheter assembly of claim 1, wherein the polymer sleeve is interlocked with one or more of the filaments of the fiber braid.

14. A catheter assembly comprising:
    a catheter shaft;
    a balloon attached to the catheter shaft, the balloon including a body and a waist portion, the waist portion having an end;
    a fiber braid including a plurality of individual filaments disposed along the body and waist portion of the balloon, the individual filaments having ends aligned with the end of the waist portion; and
    a polymer sleeve disposed on the catheter shaft, the polymer sleeve abutting the end of the balloon waist such that an outer diameter of the catheter assembly remains substantially constant along the waist portion of the balloon and an entirety of the polymer sleeve, wherein one or more portions of the polymer sleeve extend along the individual filaments of the braid.

* * * * *